United States Patent [19]

Frank et al.

[11] Patent Number: 5,133,859

[45] Date of Patent: * Jul. 28, 1992

[54] DECOUPLED FLOW AND PRESSURE SETPOINTS IN AN EXTRACTION INSTRUMENT USING COMPRESSIBLE FLUIDS

[75] Inventors: Lenore R. Frank; Christopher M. Wurm, both of Landenberg; Paul C. Dryden, West Chester; Steven J. Engel, Kennett Square, all of Pa.

[73] Assignee: Hewlett-Packard Company, Palo alto, Calif.

[*] Notice: The portion of the term of this patent subsequent to Mar. 10, 2009 has been disclaimed.

[21] Appl. No.: 487,693

[22] Filed: Mar. 2, 1990

[51] Int. Cl.$^5$ .................................. B01D 15/08
[52] U.S. Cl. .................... 210/198.2; 210/634; 210/635; 210/656; 210/659; 210/137; 210/143; 55/386; 203/49; 422/105; 422/110; 422/112; 422/261; 422/255; 422/256; 436/178
[58] Field of Search ............. 422/105, 110, 112, 261, 422/255, 256; 436/178; 210/137, 143, 634, 635, 656, 659, 198.2; 55/386; 203/49; 202/169–170

[56] References Cited

U.S. PATENT DOCUMENTS

| | | | |
|---|---|---|---|
| 3,046,098 | 7/1962 | Brasseur et al. | 436/178 X |
| 4,168,324 | 9/1979 | Roselius et al. | 426/3112 |
| 4,246,291 | 1/1981 | Prasad et al. | 426/387 |
| 4,247,385 | 1/1981 | Gorin | 208/10 |
| 4,250,331 | 2/1981 | Shimshick | 562/485 |
| 4,283,280 | 8/1981 | Brownlee | 210/198.2 |
| 4,308,200 | 12/1981 | Fremont | 260/110 |
| 4,313,828 | 2/1982 | Brownlee | 210/198.2 |
| 4,341,804 | 7/1982 | Prasad et al. | 426/387 |
| 4,345,976 | 8/1982 | Peter et al. | 203/49 |
| 4,349,415 | 9/1982 | DeFilippi et al. | 203/14 |
| 4,354,922 | 10/1982 | Derbyshire et al. | 208/68 |
| 4,363,717 | 12/1982 | Pelrine et al. | 208/108 |
| 4,375,387 | 3/1983 | deFilippi et al. | 202/169 |
| 4,388,171 | 6/1983 | Corcoran et al. | 208/8 LE |
| 4,397,731 | 8/1983 | Warzel | 208/8 LE |
| 4,400,559 | 8/1983 | Bhise | 568/858 |
| 4,406,742 | 9/1983 | Dick | 196/14.52 |
| 4,422,966 | 12/1983 | Amer | 260/97.6 |
| 4,437,938 | 3/1984 | Bhise et al. | 203/14 |
| 4,437,939 | 3/1984 | Bhise et al. | 203/14 |
| 4,438,816 | 3/1984 | Urban et al. | 166/303 |
| 4,447,310 | 5/1984 | Derbyshire et al. | 208/8 LE |
| 4,448,669 | 5/1984 | Scinta | 208/11 LE |
| 4,449,586 | 5/1984 | Urban et al. | 166/303 |

(List continued on next page.)

FOREIGN PATENT DOCUMENTS

| | | |
|---|---|---|
| 0125690 | 11/1984 | . |
| 88100485.7 | 1/1988 | European Pat. Off. . |
| 60291155 | 12/1985 | Japan . |
| 1177219 | 1/1970 | United Kingdom . |
| 2132223A | 7/1984 | United Kingdom . |

*Primary Examiner*—Robert J. Warden
*Assistant Examiner*—Amelia L. Santiago

[57] ABSTRACT

Methods and apparatus for extracting sample components from complex matrices using supercritical carbon dioxide as the principal extracting solvent are disclosed. The present invention takes advantage of the fact that the solvent power of a supercritical fluid is stepwise settable by the parameters of density, modifier concentration, and temperature. Accordingly, methods and apparatus for extracting a component from a sample using flow system having a variable and controllable flow restriction are disclosed. The methods of the present invention comprise the steps of inserting the sample into the sample container section, inputting temperature, pressure, flow rate and extraction time setpoints. The flow rate is controlled and the system pressure regulated by the variable flow restriction. The present invention contemplates opening and closing the orifice in order to control the variable flow restriction, or closing the orifice until setpoint pressure is achieved and controlling the restriction of the orifice to maintain the setpoint pressure. The present invention also discloses apparatus for the extraction of components from a sample which include means for regulating the pressure and flowrate of a supercritical extraction solvent.

34 Claims, 2 Drawing Sheets

U.S. PATENT DOCUMENTS

| | | | |
|---|---|---|---|
| 4,451,363 | 5/1984 | Brownlee et al. | 210/198.2 |
| 4,451,364 | 5/1984 | Higgins et al. | 210/198.2 |
| 4,457,812 | 7/1984 | Rado | 204/66 |
| 4,457,846 | 7/1984 | Munk | 210/656 |
| 4,474,994 | 10/1984 | Makin | 568/438 |
| 4,478,715 | 10/1984 | Goodnight, Jr. | 210/198.2 |
| 4,493,797 | 1/1985 | Avedesian | 530/507 |
| 4,495,095 | 1/1985 | Lawson et al. | 260/97.7 |
| 4,512,899 | 4/1985 | Goodnight, Jr. | 210/656 |
| 4,547,292 | 10/1985 | Zarchy | 210/634 |
| 4,568,495 | 2/1986 | Frihart | 260/428.5 |
| 4,584,140 | 4/1986 | Blewett et al. | 260/412.8 |
| 4,597,943 | 7/1986 | Sugiyama et al. | 422/70 |
| 4,601,906 | 7/1986 | Shindler | 424/195.1 |
| 4,632,837 | 12/1986 | Schutz et al. | 426/425 |
| 4,871,453 | 10/1989 | Kumar | 422/70 |
| 4,913,821 | 4/1990 | Melcher et al. | 426/178 X |
| 4,984,602 | 1/1991 | Salto et al. | 137/487.5 |

DECOUPLED FLOW AND PRESSURE SETPOINTS IN AN EXTRACTION INSTRUMENT USING COMPRESSIBLE FLUIDS

The present invention relates to methods and apparatus for extracting materials from a substance and, more particularly to supercritical fluid extraction.

BACKGROUND OF THE INVENTION

Supercritical fluids can be used as solvents in extraction instruments, chromatographs and other related instruments. The critical temperature is that temperature above which the distinction between gases and liquids disappears; there is one fluid phase for all pressures. No matter how much pressure is applied, a liquid phase cannot be condensed. The supercritical region is defined by all temperatures and pressures above the critical temperature and pressure. Supercritical fluids are a useful hybrid of gases and liquids as we commonly perceive them, possessing gas-like viscosities, liquid-like densities, and diffusivities greater than typical liquid solvents. The liquid-like density of a supercritical fluid imparts a variable liquid-like solvent power by an essentially linear function of density. This allows the solvent power, usually considered a chemical interaction, to be set ("dialed in") simply by adjusting a physical parameter, namely density or pressure. Variable solvent power is most pronounced over densities corresponding to pressures from about 0.6 times the critical pressure to pressures at which the solvent densities become nearly liquid-like.

Another important aspect of supercritical fluids is that compared to typical liquid solvents the supercritical fluid transport properties of viscosity and diffusivity allow enhanced mass transport within complex matrices, such as coal, plant or animal tissue, or packed beds. In other words, supercritical fluids penetrate better and dissolve almost as well as typical liquids. Therefore, supercritical fluids are more efficient to use for extractions of complex matrices.

Even though the solvent power of a supercritical fluid is variable, each supercritical fluid has a maximum solvent power approaching that of the substance as a liquid. Although the solvent power of a liquid is also variable and also essentially a linear function of the density, far larger increases in pressure are necessary to produce significant increases in liquid solvent power. For a typical laboratory liquid solvent such as methanol, the pressure can be lowered to atmospheric and a solution of solvent and solute is stable. Heat must be supplied to drive off solvent for solution concentration or solute drying. If a liquid with a very high vapor pressure at ambient temperatures is used, such as liquid carbon dioxide or ammonia, the solvent is readily evaporated upon solution decompression, leaving a dry, concentrated solute. However, there is a discontinuity in the density along an isotherm corresponding to tie lines between coexisting liquid and gaseous phases. Because of the discontinuity in density and solvent power essentially is made high or low, "go" or "no-go", and most of the versatility in solvent power control is lost.

In terms of mass transport properties, diffusivity is an important parameter. Liquid diffusivities cover a large range, some of which (e.g., carbon dioxide and ammonia) are almost the same as those of the supercritical fluid when the liquid is at near critical conditions. In those cases either the liquid or the supercritical fluid would suffice for efficient extraction. However, for commonly used liquids, the diffusivities are lower by a factor of 10 to 100 than for supercritical fluids and therefore these liquids are less efficient in terms of time for extraction.

Supercritical solvents are therefore superior in that they (1) allow a large continuous range of solvent powers, thus providing for selective solvation of solutes over that range, (2) provide a means of rapid and complete solvent/solute separation with minimal heat input, and (3) can decrease the time for extraction of complex matrices by a factor of 10 to 100.

Carbon dioxide is the principal extracting fluid used in supercritical fluid extraction systems since it is cheap, innocuous, readily available at high purities, and has a critical temperature of about 31° C. so it is useful for thermally labile compounds. Furthermore, it is mutually soluble with many common liquid solvents. It has been found that carbon dioxide has a solvent power similar to that of hexane. Hence, many applications exist which require great solvent power, the advantageous properties of supercritical fluids, and mild operating temperatures for thermally labile compounds. Mixtures of carbon dioxide plus modifiers can meet these requirements. As well known to those of ordinary skill, supercritical fluids can be used as solvents in extractions and chromatography; in such applications carbon dioxide is the preferred solvent. Other fluids which have critical points near ambient temperature (25° C.) such as ethane, nitrous oxide, ethylene, or sulfur hexafluoride could also function as the base solvent. The capability to utilize these alternative solvents is preferably not exploited because of the inherent danger in using these solvents.

Another way to increase the solute solubility in supercritical fluid systems is through temperature control. It has been demonstrated that for some solutes a certain minimum temperature is necessary for appreciable solute solubility in a supercritical fluid, even at maximum densities, so temperature is also a solvent power parameter beyond the simple P-T relationship with density.

The problem encountered in building extraction systems which use compressible fluids at pressures above atmospheric (ambient) is that the pressure of the fluid system is coupled with the mass flow rate of the flowing fluid. This is a result of the use of restrictors having constant geometry to achieve a pressure drop from higher pressures to lower pressures which are normally but not restricted to ambient or vacuum conditions, thus the only practical way to achieve higher pressures upstream of the restriction is to increase the mass flow rate. However, in operating these extraction systems it is highly desirable to have the same mass flow rate at all pressures, i.e., with the lower flow rates to achieve lower pressures, the time to flow a chosen net amount of fluid can be significantly longer than at higher pressures, e.g., hours vs. minutes. Therefore, in a system which can be adjusted to operate sequentially at multiple pressures (e.g., 1100 psi, 1300 psi, 1500 psi, 3000 psi, 6000 psi) at flow rates which provide the same integrated mass of expanded carrier fluid at each pressure setting the time to complete the method can be so long that the method becomes inefficient. This is particularly true in operating supercritical fluid extraction systems, as well as near-critical fluid extraction, which can be more efficient in time than extractions using conventional fluids, due to the transport properties (e.g., viscosity, diffusivity) of critical and near-critical fluids.

However, that efficiency is lost when the parameters of pressure and flow cannot be decoupled because of the hardware implementation, e.g., constant geometry flow restrictions.

It is therefore an object of the present invention to decouple the pressure and flow parameters so that they can be set and controlled independently.

In the past, operators of supercritical fluid chromatograph (SFC) and supercritical fluid extractor (SFE) instruments selected pressure and temperature parameters to set the desired density parameter indirectly. Density is usually a more meaningful parameter than pressure in supercritical (and near-critical) systems due to its simple linear relationship to the fluid's solvent power. Often, in any previous implementations of supercritical fluid systems, only pressure and temperature inputs have been allowed; calculating the resultant density or even understanding the pressure/density/temperature relationship has been left to the user, albeit occasionally prompted by abbreviated look-up tables. Therefore, in those cases, controlling the solvency has relied upon the technical sophistication and persistence of the user to apply equations of state appropriately.

The extraction of solids has typically been done manually in conventional laboratory glassware. Laboratory devices which automate the steeping of the sample in a boiling liquid solvent along with the subsequent concentration of the resultant solution are sold commercially as the "Soxtec" by Tecator. This device does not permit fractionation as part of the method; the output is not in autosampler-compatible vessels and samples are boiled at temperatures determined by the boiling points of the extracting solvents, which can be detrimental to thermally labile compounds. Recently, several companies have offered instruments based on using supercritical fluids: Milton Roy, Suprex, CCS, Lee Scientific/Dionex, and Jasco. The implementations by these companies are not exceptionally sophisticated or automated; they require various degrees of manual intervention. In these implementations, the full capability of using supercritical fluids for quantitative extraction is not realized Thus, there exists a long-felt need to design an instrument which could be used to isolate various materials from solid samples using supercritical fluid technology. Either the isolated materials (extract) or the material remaining (raffinate) could be of interest. The process of isolation is referred to as extraction. The need also existed to automate the extraction of solids, since typically the procedures are manually intensive. In the business of preparing samples for analytical instruments, it would be highly desirable to automate sample preparation of raw samples to obtain a form compatible with introduction into typical analytical instruments used in analytical laboratories worldwide. The extraction of solids is often accompanied by other manipulations such as fractionation (e.g., by column chromatography), concentration, solvent exchange, and reconstitution. A method comprised of these generic manipulations may actually consist of many (ranging from several to hundreds) of manual steps. It would therefore be desirable to produce an instrument which replaced the five mentioned generic manipulations so that the only step required was to present a sample to the extraction instrument and receive fractions of isolated material in vessels compatible with the autosamplers of analytical instruments.

Improvements in the isolation of selected material from solid samples and the automation of the generic manipulations of processes such as extraction, fractionation, concentration, solvent exchange, and reconstitution are clearly desirable goals. It would be desirable and of considerable advantage to use a technique different from the traditional laboratory manipulations known to those of ordinary skill if such a different technique provided superior performance in any of the following areas: quantitation, repeatability and reproducibility, speed, automation, automatability, health hazard reduction, or cost reduction (materials and labor).

Ideally, an extraction instrument would be a stand alone module, that is, a component instrument within an integrated system. In such systems it is also highly desirable t provide robotic accessibility for inputting the sample and retrieving the fraction in an automated fashion. An important aspect of any extraction system therefore lies in its upgradability for automating the sample input (i.e., adding an autosampler for solid samples) and automating the fraction output (i.e., fraction collection with further chemical manipulation and large-scale queueing); an external pump module for blending extraction fluid composition could also be a future addition.

Another improvement in the utility of extraction systems would be the use of standard input and output containers for the sample which is input and the fraction solutions which are output. The instrument would accordingly be provided with a multiple sized extraction chamber which accepts the solid samples.

An improved extraction instrument would also incorporate an automated "method", with a method being defined as that sequence of manipulations associated with any one sample. Examples include, but are not limited to, valve actuation, thermal zone setpoint changes, extraction fluid solvent selection, reconstitution solvent selection, flow path selection, fraction output destination, density/pressure setpoint changes, flow rate setpoint changes. Such an automated extraction instrument would also provide automatic selectable output destinations within a method, and from method to method; automatic selectable inputted extraction fluid composition within a method and from method to method; and automatic selectable rinse solvents for the solvent exchange/reconstitution emulation processes within a method and from method to method.

SUMMARY OF THE INVENTION

The present invention provides a sample preparation device which extracts sample components from complex matrices using supercritical carbon dioxide as the principal extracting solvent and presents the resulting extract in a user-chosen sample collection vessel (autosampler vial, bulk vessel, cuvette, etc.) with the autosampler vial being directly compatible with automatic injection systems of other analytical instruments (CC, LC, SFC). The present invention replaces traditional preparative procedures such as solvent extraction, Soxhlet extraction, liquid/liquid extraction, concentration, and evaporation. With the solvent power stepwise settable by the parameters of density, modifier concentration, and temperature, the supercritical fluid extractor can mimic column chromatography sample fractionation in some applications.

Accordingly, methods of extracting a component from a sample using fluid flow system apparatus comprising control apparatus, at least one element having a variable and controllable flow restriction and a sample container section are disclosed. The methods of the present invention comprise the steps of inserting the sample into the sample container section, inputting temperature, pressure, flow rate and extraction time setpoints into a control apparatus and providing pressurized fluid. By directing the fluid to a pump which injects the fluid into the flow system apparatus at the input flow rate setpoint the extraction process is initiated. The system pressure is sensed as fluid is pumped into the system and the variable flow restriction is regulated to achieve and to maintain the setpoint pressure. Extraction is accomplished by directing fluid through the sample at the setpoint flow rate and directing a fluid mixture leaving the sample container section to an expansion nozzle section. Preferably, the methods of the present invention include maintaining the controlled setpoints of flow, pressure, and temperature until the input extraction time is achieved. In certain embodiments, the step of inputting the setpoints is repeated to generate a method of extraction which varies those parameters in the order prescribed. The methods of the present invention contemplates opening and closing the orifice in order to control the variable flow restriction, or closing the orifice until setpoint pressure is achieved and controlling the restriction of the orifice to maintain the setpoint pressure.

The present invention also discloses apparatus for the extraction of components from a sample. Preferably, a pump for liquefying a gas, comprising a pump motor and a pump motor speed control are provided along with means for regulating the pressure of the output of the pump to a setpoint pressure. Pressurized fluid to an extraction section means for retaining a sample by a flow system. The apparatus also comprises a nozzle having a variable orifice and a pressure transducer for providing a pressure signal connected to a regulator feedback loop from the pressure transducer which provides a signal to the pump motor speed control. The pressure drop across the nozzle permits the recovery of dissolved material precipitating from the expanding fluid, while the parameters of flow and pressure are decoupled. In one alternate embodiment the regulator feedback loop controls the speed of the pump to maintain the pressure of the fluid at a predetermined value, and the nozzle having a variable orifice is set to create a restriction which limits the mass flow rate of the pressurized fluid to a predetermined value. In another alternate embodiment, the pump comprises a metering pump for providing a controlled mass flow rate, and the nozzle having a variable orifice is set to create a restriction which maintains the pressure of the pressured fluid to a predetermined value.

Thus in a preferred embodiment of apparatus for the extraction of components from a sample made in accordance with the present invention are disclosed. The system described comprises one or more sources of solvent fluid and one or more extraction solvent fluid input ports connected to a high pressure pump. A pressure transducer measures the pressure of the fluid delivered by the high pressure pump. An extraction chamber flow system is preferably provided comprising an extraction chamber for retaining the sample in the flow stream of the fluid and a sample input module for containing the sample in the extraction chamber. A bypass flow system is also provided which routes fluid flow around the extraction chamber section. These flow systems are joined by a means for merging the bypass flow system and extraction chamber flow systems. In order to isolate the extracted component, the present invention utilizes a sample collection means for separating the extracting solvent fluid from components from the sample, comprising at least one nozzle and trap subassembly. A flow transducer is also preferably incorporated, as well as at least one sample collection vessel. In this preferred embodiment of the apparatus of the present invention, pressurized liquid is flowed through the sample under independently predetermined and controlled conditions of flow and pressure and the pressurized fluid dissolves one or more selected components from the sample, and the components are collected by the sample collection vessel. Numerous variations and additions to the basic apparatus described are set forth in detail below.

Finally, the present invention also discloses methods for operating a supercritical fluid extraction systems comprising a pressure and thermal control systems which are programmable by a user to predetermined values and regulate the system to maintain such values. First, the user inputs the operating fluid setpoint density and zone temperatures and the system rounds the setpoint density to a value which is distinguishable as a setpoint at the given region of the equation of state for the fluid. Next, the system calculates the operating pressure corresponding to the setpoint density using known relationships between these variables. The user is notified if the values of density and temperature result in pressures outside the operating region of the instrument and the operating pressure and other values are then displayed. Finally, the system transmits values to the pressure and temperature control systems maintaining the setpoint density within the design specifications during the extraction process.

DETAILED DESCRIPTION OF THE PREFERRED EMBODIMENTS

In accordance with a first aspect of the present invention, flow and pressure setpoints may be decoupled. A user initiates a method for supercritical fluid extraction in accordance with the present invention by inserting the sample in the flow system and inputting temperature control setpoints and a control pressure or a density setpoint. If the latter is chosen the control pressure must be calculated using the density setpoint entry. The operator then inputs a control flow rate, a length of time for the extraction—which determines how long the extracting fluid will flow through the sample—along with system parameters time. The method of the present invention then repeats the parameter setpoint selection for all steps to generate a complete extraction cycle which varies those parameters in the order prescribed by the user. By issuing a "Start" command, the instrument then pursues the following steps: (1) withdrawing fluid, either as a gaseous layer or a liquid layer, from standard gas cylinders with their contents at pressures above the ambient or atmospheric pressure; (2) directing the withdrawn fluid to a pump which is electronically controlled to deliver fluid to the rest of the extraction system at the flow rate selected; (3) sensing the system pressure as fluid is injected into the system; (4) controlling the nozzle orifice to be closed until setpoint pressure is achieved by the injection of fluid into a closed system; (5) initiating time measurement in order to compare to setpoint extraction time; (6) controlling the nozzle orifice to an appropriate degree of restriction thereby maintaining setpoint pressure once it is achieved and fluid injection into the system continues at the setpoint flow rate. Fluid is then directed through the flow path selected through the sample container section. The system then directs the fluid mixture leaving the sample container section to the expansion nozzle section, and continues to maintain all controlled setpoints of flow, pressure, and temperatures until the extraction time input has elapsed.

Figure 1:
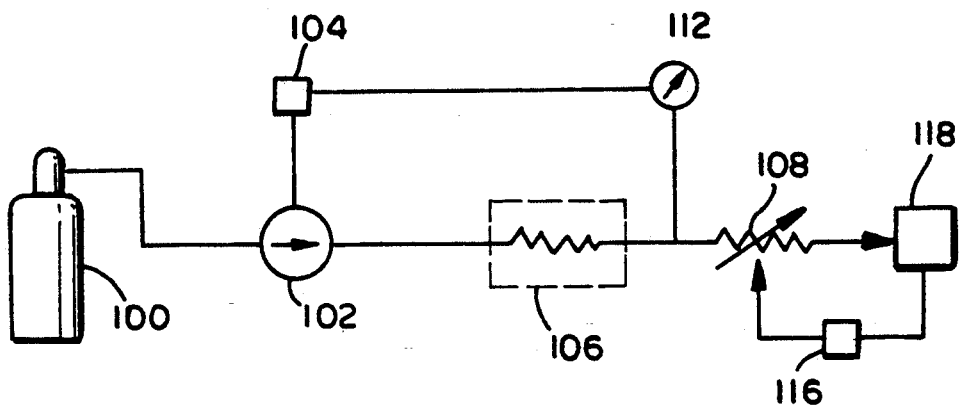
FIG. 1 is a simplified schematic representation of an extraction system made in accordance with the present invention.

Referring now to FIG. 1, an embodiment of the extraction system of the present invention using supercritical and near-critical fluids is shown. The system first pressurizes carbon dioxide or other fluids or fluid mixtures from gas cylinders 100 using a pump 102 which has a regulator 104 which controls the setpoint pressure. The flow system directs the pressurized fluid to an extraction section 106 holding a sample which contains components to be isolated. The system then directs the fluid solution to a nozzle 108 where it is depressurized to lower (e.g., atmospheric) pressures. In the embodiment shown, the nozzle 108 has a variable orifice set to create a restriction which limits the mass flow rate. Achieving setpoint pressure is accomplished by regulating the speed of the pump 102 using the regulator 104; both decoupled parameters are set independently. The regulator 104 is part of a feedback loop from a pressure transducer 112 which provides a signal to the pump motor speed control 104 to gain operating stability at the selected pressure setpoint. A flow transducer 118 is provided as part of a control loop 116 which regulates the physical restriction of the variable orifice of the nozzle to control the setpoint flow rate.

Figure 2:
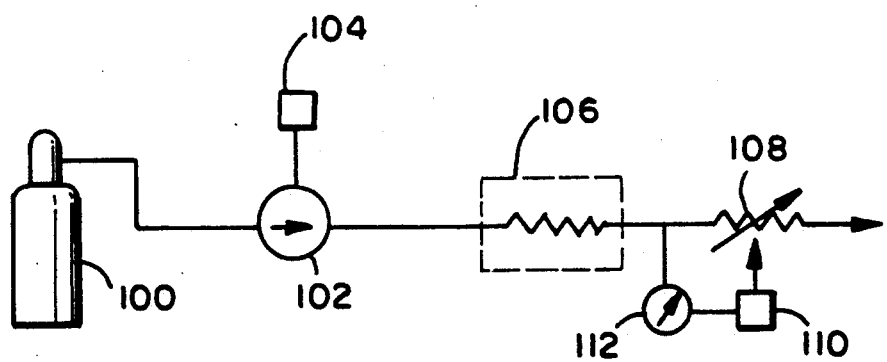
FIG. 2 depicts another simplified schematic representation of another embodiment of the present invention.

In a preferred embodiment of the present invention depicted in FIG. 2, fluid is pumped by a metering pump 102 at a given flow rate to supply the rest of the flow system with a controlled mass flow rate. Again, fluid flows through the sample in an extraction section 106 which is immersed in the flow path, dissolves material from the sample, and goes through a pressure drop at the nozzle 108. The nozzle 108 functions as the region causing the pressure drop in the high pressure solution to recover dissolved material precipitating from the expanding extraction fluid, as well as a back pressure regulator for the pressurized system. A control loop 110 using a signal from a pressure transducer 112 controls the physical restriction in the nozzle 108 to maintain a setpoint pressure for the whole range of mass flow rates metered out by the pumping system ranging from no flow to about 4 g/min. As will be understood by those of ordinary skill, a variable annular orifice nozzle 108 may be implemented in a variety of ways; for example, a modified needle valve can be constructed, with particular attention paid to expansion region design.

When using supercritical fluids the parameter of density, which is a function of pressure and temperature, is directly related to solvent power (solvency) of the fluid; therefore, solvent power is adjustable and selectable by setting and regulating 2 of the 3 parameters. Since pressure transducers are common and density transducers at the operating conditions of typical extraction devices are not, it is preferable to select the desired operating density and temperature, calculate the appropriate operating pressure, control to that pressure.

The independent control of pressure and flow enables the chemist to vary the extracting fluid solvent power by choosing operating pressure and to vary the rate (or efficiency) of extracting fluid throughput by varying the pump flow rate. With the parameters decoupled, the user can extract over the range of both parameters for a selected amount of time, i.e., net amount of extraction fluid. Essentially, all these parameters are now independent: flow rate, pressure, and time. In certain embodiments of the present invention, temperatures of many sections of the flow system are also controlled independently as a fourth parameter.

As will be readily appreciated by those of ordinary skill the present invention provides a significant advance in the development of supercritical fluid chromatography (SFC) by maximizing chromatographic efficiency. Typical prior embodiments of SFC extraction instruments employed fixed restrictors (holes, lengths of capillary tubing, frits, etc.) to effect the necessary pressure drop from operating with supercritical and near-critical carrier fluids (also known as mobile phases). The restrictors typically had diameters in the order of microns. In the application of SFC, the exploitation of the parameters of density (pressure), flow rate, and temperature is as important as doing so in supercritical fluid extraction (SFE). With the fixed restrictors, chromatographers were forced to achieve operating pressures by varying the flow rates. This is undesirable, however, since in chromatographic separations, flow rate is an important parameter in separation efficiency. Often the flow rates necessary to achieve high pressures are far too high to be operating at the most efficient chromatographic region, i.e., the minimum of a van Deemter curve. Independent control of pressure (density) and flow rate, as disclosed by the present invention therefore allows the appropriate chromatographic operation.

Figure 3:
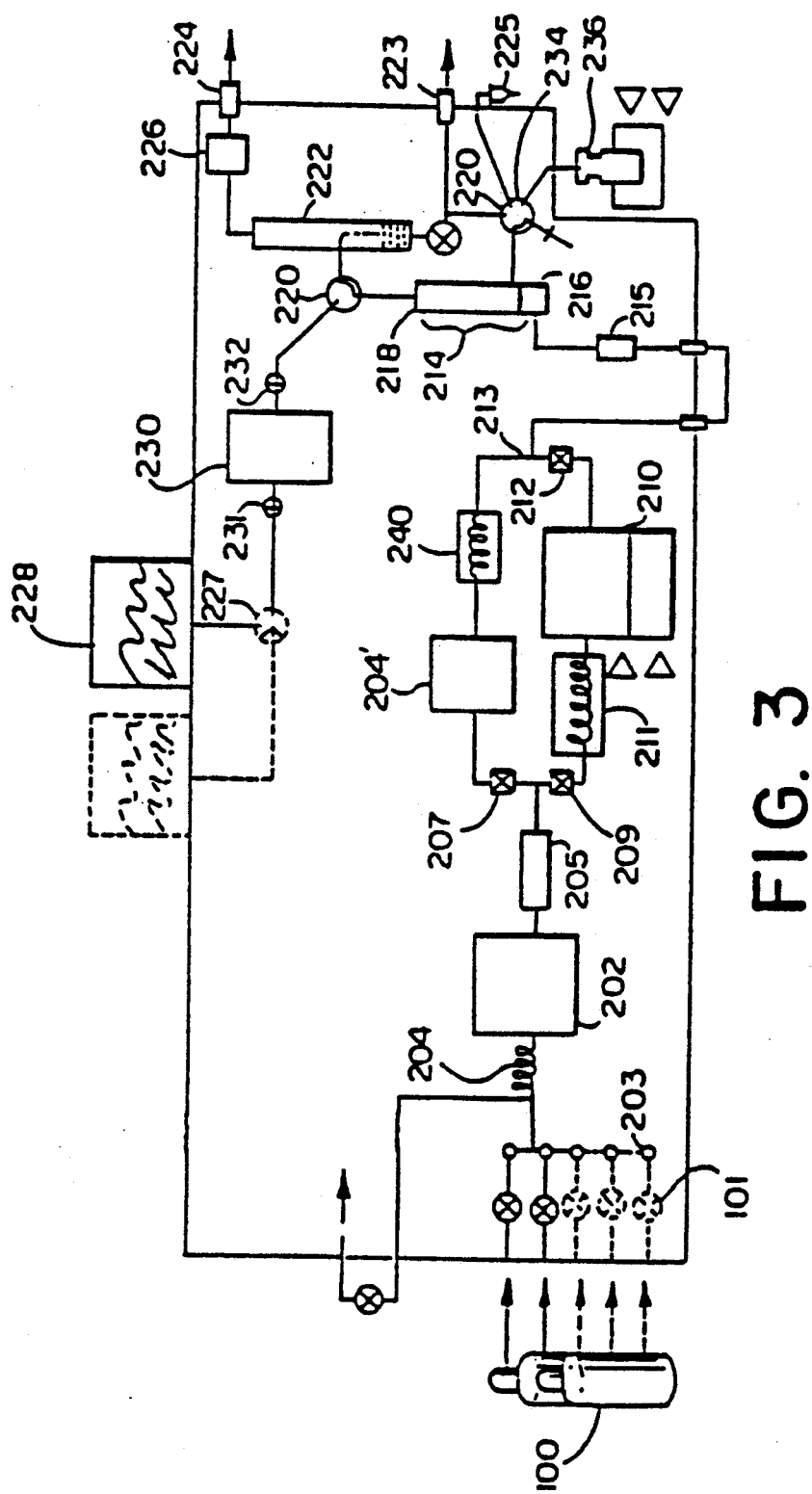
FIG. 3 shows a schematic representation of a preferred embodiment of an extraction instrument made in accordance with the present invention.

Referring now to FIG. 3 a preferred embodiment of the apparatus of present invention for the extraction of components from solids, semi-solids, and small-quantity liquids is provided. The apparatus comprises multiple extraction fluid input ports from gas cylinders 100, each having valving 101 and an, in some instances an accompanying check valve 203 located downstream, to provide port selection of multiple-to-one, as desired. A heat exchanger 204 for control of fluid temperature upstream and just prior to injection into the pump may also be included. The solvent then flows through a high pressure pump 202 which can be thermally controlled to give desired fluid compressibility within the pumping chambers. To attenuate the pressure ripple due to pumping of the fluid a pulse damper 205 is provided downstream from the pump 202. The flow is then divided into two sections, referred to as the "bypass" and "chamber" sections. Valving 207,209 is supplied to direct flow to either, both, or neither of the two sections noted above.

The chamber section of the flow system is regulated by the lower valve 209, shown in FIG. 3. A preheater 211 may again be included in this section of the flow system in order to regulate the temperature of the solvent. An additional preheater 240 may also be provided in the bypass section. The fluid then flows into the chamber 210 where extraction takes place. As shown schematically, the chamber of the present invention is preferably actuated between two positions. This actuation permits the chamber to be automated and to include apparatus for automatically creating the high pressure seals necessary between the chamber 210 and the vessel containing the sample.

Since the chamber is actuated between the two positions shown, flexible couplings, including tubing for the fluid connections and flexible electronic connections for thermal, control and power signals are provided since it is necessary that the apparatus of the present invention supply fluid to an actuated section.

The sample input module contained within the chamber 210 preferably allows a sample to be inserted in the flow stream via the extraction chamber 210, with subsequent achievement of all necessary seals made by the actuation provided. The design of the sample input vessel interface and actuators preferably permits various sizes of cylindrical containers to be accommodated. The sample input vessel, referred to as a "thimble," preferably is a common vessel in an automated bench, permitting the same vessel to serve as a sample transport vessel, as a part of filtering apparatus.

As pointed out above, the flow system of the present invention includes a bypass section, controlled by the upper valve 207, shown in FIG. 3. The bypass section routes fluid flow around the extraction chamber section 210 containing the sample to allow equilibration of all controlled setpoints, before sampling of the contents of the solution from the chamber/cylindrical container occurs. The pressure of the fluid delivered by the high pressure pump is measured by a pressure transducer 204, which is illustrated as being located within the bypass section. However, in other embodiments of the present invention, the transducer 204 may be located elsewhere, or one or more additional transducers be included in order to more completely monitor the pressure at various points in the flow system.

Meaningful control of the solvent power of the extracting fluid via pressure/density is achieved using the pressure transducer 204. As will be understood by those of ordinary skill, the design of such a pressure transducer 204 must meet appropriate accuracy and precision specifications. The transducer is preferably mechanically chosen to minimize dead volume to the fluid stream and is placed close to a back pressure regulation subassembly and relatively close to the exit of the chamber 210 in order to minimize pressure drop to both of those sections. Those of ordinary skill will readily understand that FIG. 3 is thus a schematic of the present invention and the relative placement of the components described is determined by the operating specifications of the system and the performance of the components chosen.

The bypass and extraction chamber flow paths described above are subsequently merged together at a juncture 213 to flow into the nozzle-trap subassembly 214 through the use of appropriate valving and filtering. The apparatus of the present invention also includes valving to isolate the high pressure flow path from the low pressure rinse section. To minimize the failure of the nozzle assembly 214 due to particulates, a filter 215 is preferably provided directly upstream of the nozzle/trap subassembly 214.

The flow is then routed to the subassemblies which make up the sample collection section of the system in which the high pressure fluid comprising pure extraction solvent, mixed extraction solvents, and/or mixtures of extracted components dissolved in the extracting solvent encounters a pressure drop in the nozzle subassembly 216. The pressure drop allows splitting the extracting solvent from dissolved components, since high vapor pressure liquids such as liquid carbon dioxide or subcritical or near-critical mixtures of fluids such as carbon dioxide plus methanol expand upon encountering a pressure drop.

The nozzle subassembly 216 also provides a back pressure regulation function as part of the pressure control loop and a thermal control zone. However, flow control is independent of pressure/density control. In a preferred embodiment of the apparatus of the present invention, flow control is provided by a pump 202; however, in other embodiments, as explained above with references to FIGS. 1 and 2, it is possible to use the nozzle 216 for flow control and have the pump 202 control the pressure and density.

For those fluids which remain liquid upon encountering the pressure drop at the nozzle 216, a trap subassembly 218 is operated to vaporize them downstream. The trap subassembly 218 provides a section to baffle the expanding flowing gas stream in which precipitating extracted components are entrained. The trap subassembly 218 may be filled with porous or granular material which is either inert or which has some chemical activity, such as adsorbents, or some chemical functionality, such as stationary or bonded liquid phases. Those of ordinary skill will readily understand that the filling or packing used within the trap subassembly 218 is a parameter which the user may exploit for fractionation.

The trap subassembly 218 is also an independently controlled thermal zone which may be operated between subambient and heated conditions. For those extraction fluids not vaporized by encountering a pressure drop, the thermal control of the trap subassembly 218 is used to vaporize such fluids as, for example, hexane, or modifiers used to make modifier-carbon dioxide mixtures.

The apparatus of the present invention preferably includes an actuated diverter valve(s) 220, 234 have positions allowing direction of exhausting vapors to vent/waste positions during extraction, and to direct rinsing solutions to collection hardware of various sizes, or to vent/waste during rinse sequences. The actuated diverter valves 220, 234 preferably perform valving actions while having minimal dead volume. Valving is also provided to direct the rinse fluids streams or exhausting extraction fluids to different destinations. A first destination is a splitter column 222 which ends in both a liquid waste stream 223 and a gaseous vent 224. A second destination is a remote port 225. Preferably, the splitter column 222 is controlled at low temperatures and uses demisting components to separate liquid modifiers from the base vaporized extracting fluid or to collect liquid solvents.

A flow transducer 226 or rotameter is preferably connected to the top of the splitter column 222. The splitter column is also connected to the actuated diverter valve 220, which comprises ports by which rinse solvents are supplied. A valve 227 (or multiple valves) is supplied to select rinse solvent stream from one or more rinse solvent reservoirs, which supply the rinse solvent pump 230, which can withstand system pressure. The rinse solvent pump 230 preferably has a variable dispense rate appropriate for liquid-chromatographic type zone movement and can be directed to supply user-selected collection volumes at the chosen destination. The rinse solvent pump 230 may be configured with an active inlet valve 231 or an active outlet valve 232 for more reliable operation. These valves may be typical check valves or switching valves.

Thus, under selected conditions, rinse solvent is directed through the pump 230 and the diverter valve 220 into the trap subassembly to dissolve precipitated components and move them to the fraction collection destination chosen by the user. The direction of the rinse solvent through the trap can be foreflushed or backflushed relative to the flow of the extraction fluid during the extraction step. FIG. 3 illustrates a backfkushed system, although foreflushed is also a preferred embodiment of the present invention.

The trap subassembly 218, is connected to liquid waste port 223, remote port 225 and automatic liquid sampler vials 236, preferably in a queue by an actuated valve 234. The valve 234 supplies a sample collection vessel 236, which is actuated as explained above with reference to the extraction chamber 210 in order to facilitate automation. Thus, in a preferred embodiment, the apparatus of the present invention also comprises a queue which can collect multiple fractions in sample collection containers such as the autosampler vials which are typically used in gas and liquid chromatographs.

While the primary form of sample which the apparatus of the present invention accept comprise solid samples, it is possible to introduce small quantities (i.e., microliter to milliliters in volume) of liquid by distributing the liquid upon solid supports such as filter paper, adsorbents, or powders. Similarly, semi-solids such as fats and creams can be input.

In other embodiments of the present invention, it may be desirable to include one or more further nozzle/trap subassemblies additional to the nozzle/trap subassembly 214 described above with reference to FIG. 3. Such additional nozzle/trap assembly/assemblies would either be incorporated into the apparatus of the present invention or resident on other instruments coupled thereto. In some cases, an additional nozzle may be the only additional subassembly. In other embodiments, the nozzle and/or trap subassemblies resident on other instruments may be substituted entirely for those preferably provided as a part of an extractor made in accordance with the present invention. Additionally, the hardware of the nozzle and trap subassemblies may be specialized to assume functions within the apparatus of the present invention or the instruments on which they are resident, examples include, injection ports on gas chromatographs, precolumn or heart-cutting on liquid chromatographs.

Another modification to the apparatus disclosed is the inclusion of means for hooking up additional connections between the remote port 225 and/or the trap exits 223,224 and other analytical instruments—e.g., particularly liquid chromatographs, Uv/VIS spectrophotometers, and liquid samplers—such that the fraction rinsed from the trap 218 can be directed to those instruments for further manipulation and subsequent analysis.

Similarly, the apparatus disclosed in FIG. 3 can be modified to provide sampling of the fluid solution leaving the extraction chamber 210 prior to recovery of solutes in the nozzle/trap subassembly 214 or prior to being directed to other instruments. For example, the sampled stream, possibly at high pressure, may be directed to a UV/VIS spectrophotometer or through sampling valves on a variety of other analytical instruments such as liquid chromatographs, supercritical fluid chromatographs, gas chromatographs.

As set forth above with reference to FIG. 3, the trap 218 may be filled with a packing material. However, alternate embodiments of the apparatus of the present invention may include additional regions containing some chemically active packing material (e.g., typical liquid chromatographic column packing materials, adsorbents, or other porous material) and additional thermal zone control and hardware an additional valving to control the fluid direction to such regions. The addition of such apparatus permits the apparatus to be used to provide fractionation of the mixture of the solution leaving the extraction chamber 210 containing the sample before that solution encounters the nozzle and/or trap subassembly 214. Flow through the chamber and bypass regions discussed above is coordinated along with thermal zone operation to deposit sample material in the fractionation zone and then selectively remove components from that zone. The components are collected in any of the apparatus configurations outlined above.

The queue of sample collection vessels 236 described above may be supplemented with additional fraction queues which provide for any of the following functions: collection of more autosampler vials, reading and/or writing of labels on the autosampler vials (bar code labels), further fractionation of the components in the fraction solution by solid phase extraction or other typical wet chemical manipulations, and typical wet chemical manipulations and reactions encountered in analytical laboratories to obtain solutions appropriate for the selected analytical method including quantitation.

Also, automated apparatus can be provided for placing the extraction containers in the extraction chamber 210, removing extraction containers from the chamber 210, replacing the extraction containers in a queue/storage area. Reading and writing labels on the extraction containers (sample input vessels) may also provided in such embodiments In certain embodiments the pump 202 may be modified by providing a pump which is capable of operation for isocratic, binary or ternary solvent delivery to the extraction instrument to blend fluids and fluid mixtures, particularly those which are ordinarily liquid at ambient conditions. The base extracting fluid is coupled via appropriate tubing and valving and coordinated actuation is provided via a workstation or other computer-based controller which can issue commands to the solvent valves and pump. Thus in certain embodiments, the addition of additional pumping channels to blend fluids and fluid mixtures (particularly those which are ordinarily liquid at ambient conditions) with the base extracting fluid to form multicomponent extracting solvents may be accomplished by incorporating further pumps and valving within the extractor instrument to achieve a mixture for the extracting fluid.

Most preferably, valves are provided to select the rinse solvent stream and to supply the rinse solvent pump. As described above, the rinse solvent pump can withstand system pressure and has a variable dispense rate appropriate for liquid-chromatographic type zone movement. Valving is provided which can be direct fluid to supply user-selected collection volumes to chosen destination.

Finally, as will be understood by those of ordinary skill in the design of such systems, the instrument of the present invention can be coupled with other instruments and techniques in a manner referred to as hyphenation. Examples of hyphenation which are contemplated by the present invention are: high pressure solid phase extraction coupled with supercritical fluid extraction of samples; solid phase extraction as a precursor to supercritical fluid extraction; low pressure fractionation in some embodiments as refined as solid phase extraction on the extract collection trap 218 after the supercritical fluid extraction of the sample; rinse solvent interface (i.e., the reconstitution solvent) to other instruments; high pressure stream sampling between the chamber 210 containing the sample and the sample collection subassembly 214 (the nozzle 216 and trap 218), which also functions as the pressure control mechanism so that other devices can monitor or take samples from the high pressure stream; use of multiple sample collection subassemblies; use of a command set which has the features of (a) providing concatenation with other commands from the user to other destinations so that sequences from the extractor instrument can be coordinated with other sequences and (b) primitive commands from which sequences could be built.

It is contemplated that the present invention may be utilized in conjunction with other analytical instruments, some of which may include a nozzle and/or trap section as described above with relation to the present invention. Such analytical instruments include gas chromatographs, liquid chromatographs, and supercritical fluid chromatographs. Additionally, the present invention may also comprise means for fractionating the extract from the sample before encountering the nozzle. Such a fractionator will utilize valving 300 and thermal control means associated with the extraction chamber 210 and the nozzle 216.

The engineering of the instrument of the present invention applies an understanding of the important parameters and limitations in various areas: supercritical fluids, (supersonic) expansion of fluids, collection/reconstitution of extract, pumping of compressible fluids, setpoint control. As set forth above, the system utilizes a fluid compressibility algorithm for pumping the solvent and utilizes a pressure-volume-temperature algorithm allowing density to be input as the relevant parameter for solvent power (vs. pressure) while providing for decoupled flow and pressure/density control. Preferably, the system permits bypass and/or dilution mode flow to occur. In certain embodiments, extraction solvent fluid composition selection is provided by multiple inputs; in other embodiments extraction fluid composition selection is provided by additional pumping channels. In the embodiment described above which incorporated appropriate valving and controlling software both static extraction and dynamic flow extraction can be achieved. The design of the present invention also provides multiple zone thermal/pressure control to specifications which were based on understanding the impact of these parameters upon density -control, particularly for the critical, near-critical and supercritical regions.

The present invention also provides methods for the incorporation of a density/pressure/temperature algorithm into a user interface for setpoint entry and subsequent parameter control. This aspect of the present invention allows the operator to input density as a parameter to instrumentation which uses conventional pressure transducers as part of the electronic control loop to maintain pressure (and, hence, density) at a user-specified temperature. As explained above, at this time, no density transducers are appropriate for general instrumentation for an electronic control loop to control density directly, but could be incorporated into the present invention.

The present invention also provides a method for operating a supercritical fluid extraction system having an electronic pressure control system along with a thermal control systems by which a user can input a desired density to maintain setpoint density without having to regulate the flow rate of the extracting fluid to achieve the density setpoint. First, the operating density and zone temperatures are input via a user interface. The setpoint density is then rounded to a value which is distinguishable as a setpoint given the control capability of the thermal and pressure control loops at the given region of the equation of state. Next, the system calculates the corresponding operating pressure and notifies the user if the combination of the density and temperature setpoints results in pressures outside the operating region of the instrument. The system will then display the corresponding operating pressure to the user so all parameters are visible. Finally, pressure and temperature setpoints are transmitted to the appropriate control loops to maintain density during the extraction or other cycle.

The methods disclosed provide a means to allow the operator to focus on the more significant parameter of density in selecting the parameter setpoints for instrument operation of a supercritical fluid extractor. The operator thus avoids having to use look-up tables, necessarily requiring interpolation among entries for those densities at temperatures and pressures not represented in the table. In operation, the system provides feedback to the user immediately when a specified density cannot be reached due to exceeding the operating boundaries of the interactive parameters—e. g., if some high density and high temperature combinations exceed possible delivery pressure.

Thus, the present invention avoids the user's inputting a parameter (pressure) whose non-linear relationship to solvency is not intuitive and changes significantly depending upon the chosen isotherm when solvency (solvent power) is the key parameter in the instrument. The importance of density as a parameter is instead instilled in new users as well as the discipline of using it.

Based on the equation of state of a particular substance, a control program is created to allow the input of density, with the subsequent calculation of the corresponding pressure at a given temperature. Such a program is a more automated approach to a look-up table, as well as a tool to explore design margins and specifications (temperature and pressure ripple impacting resultant density).

Not only does the present invention encourage the use of density as a more nearly directly proportional solvent power parameter, but also it indirectly prompts users to utilize more conservative setpoint values of pressure, thus leading to longer equipment lifetimes. This last point arises from the "S" shape of isotherms in which, at higher densities, very large increases in pressure result in very small corresponding increments in density.

Although certain embodiments of the present invention have been set forth with particularity, the present invention is not limited to the embodiments disclosed. Accordingly, reference should be made to the appended claims in order to ascertain the scope of the present invention.

What is claimed is:

1. Apparatus for the extraction of components from a sample, the apparatus having independently selected levels of extraction fluid flow and pressure comprising:
   a pump for liquefying a gas to create a pressurized extraction fluid output stream, comprising a pump motor speed motor and a pump control;
   means for regulating the pressure of the output stream of said pump to a selected setpoint pressure;
   fluid conduit means for directing the pressurized extraction liquid output stream from the pump to an extraction chamber flow system comprising an extraction chamber for retaining a sample, and an outlet;
   a nozzle having a variable orifice and an inlet connected to the outlet of the extraction chamber flow system;
   a pressure transducer for providing a pressure signal indicative of the pressure of the extraction fluid at the outlet of the extraction chamber flow system; and
   a feedback loop from said pressure transducer which provides a signal to maintain the selected setpoint pressure,
   whereby the pressure drop across said nozzle permits the recovery of dissolved material precipitating from the expanding pressurized extraction fluid.

2. The apparatus of claim 1, wherein said regulator feedback loop controls the speed of said pump to maintain the pressure of said pressurized fluid at a predetermined value, and said nozzle having a variable orifice is set to create a restriction which limits the mass flow rate of the pressurized fluid to a predetermined value.

3. The apparatus of claim 1, wherein said pump comprises a metering pump for providing a controlled mass flow rate, and said nozzle having a variable orifice is set to create a restriction which maintains the pressure of the pressured fluid at a predetermined value.

4. Apparatus for the extraction of components from a sample comprising:
   one or more sources of extraction fluid;
   one or more extraction fluid input ports;
   a pump connected to said sources by said input ports for creating at least one pump output stream comprising a supercritical fluid exiting through an outlet of said pump;
   a pressure transducer to measure the pressure of the pump output stream;
   an extraction chamber flow system connected to the pump output stream comprising an extraction chamber for retaining a sample in a stream of extraction fluid defined in said chamber and a sample input module for containing the sample in the extraction chamber;
   a bypass flow system connected to the pump outlet which routes the extraction fluid around said extraction chamber;
   means for merging the bypass flow system stream and an extraction chamber flow system stream together into a merged stream;
   sample collection means for separating the extraction fluid from components extracted from said sample, connected to the merged stream and comprising at least one nozzle having a nozzle
   outlet connected to a trap having at least one trap outlet;
   a flow transducer; and
   at least one sample collection vessel connected to the liquid trap outlet;
   whereby pressurized extraction fluid is flowed through the sample under independently predetermined and controlled conditions of flow and pressure and the pressurized extraction fluid dissolves one or more selected components from the sample, said dissolved components being collected by the sample collection vessel.

5. The apparatus of claim 4 further comprising means for directing rinse solvent through the trap to dissolve precipitated components and move them to a fraction collection destination chosen by the user.

6. The apparatus of claim 5, wherein the trap is connected to the means for conducting rinse solvent, whereby the direction of the rinse solvent through the trap is foreflushed relative to the direction of the flow of the extraction fluid during the extraction step.

7. The apparatus of claim 4, further comprising means for defining a queue for collecting multiple fractions in a plurality of sample containers.

8. The apparatus of claim 7 wherein said sample containers are autosampler vials used in gas and liquid chromatographs.

9. The apparatus of claim 4, further comprising a splitter column controlled at low temperatures and using demisting components to separate liquid modifiers in the solvent fluid from vaporized solvent fluid and collect liquid solvents.

10. The apparatus of claim 5, wherein said rinse solvent pump comprises means for creating a variable dispense rate whereby the flow of the solvent effects liquid-chromatographic type zone movement and wherein said rinse solvent pump is selectively connected to at least one of a plurality of collection volumes.

11. The apparatus of claim 4, wherein said pump comprises a means for controlling the fluid compressibility within its pumping chambers.

12. The apparatus of claim 4, further comprising a heat exchanger for control of the fluid temperature of the pump output stream and disposed between the pump and the extraction chamber.

13. The apparatus of claim 4, further comprising a pulse damping means to attenuate the pressure ripple due to the pumping of the fluid.

14. The apparatus of claim 4, wherein said extraction chamber comprises means for actuating the chamber to be opened and closed and further comprises flexible couplings between the pump outlet and the extraction chamber.

15. The apparatus of claim 4, wherein said trap is filled with porous granular material.

16. The apparatus of claim 15, wherein said porous material is inert.

17. The apparatus of claim 15, wherein said porous material has some chemical activity.

18. The apparatus of claim 16, wherein said porous material comprises an adsorbent.

19. The apparatus of claim 4, further comprising additional means for connecting the fraction rinsed from the trap to other analytical instruments for further manipulation and subsequent analysis.

20. The apparatus of claim 4, further comprising means for sampling the fluid solution leaving the extraction chamber prior to recovery of solutes in the nozzle and the trap.

21. The apparatus of claim 4, further comprising fractionation means for retaining chemically active packing material to be used to provide fractionation of the solvent fluid in the merged stream and disposed between the extraction chamber and the nozzle.

22. The apparatus of claim 4, a fraction queue means for manipulating a plurality of the sample collection vessels.

23. The apparatus of claim 4, further comprising means for reading and writing labels on the sample collection vessels.

24. The apparatus of claim 4, further comprising a pump means for providing a plurality of solvent fluid streams to the extraction apparatus.

25. The apparatus of claim 1, wherein said nozzle is disposed within a further analytical instrument.

26. The apparatus of claim 25, wherein said analytical instrument is a gas chromatograph.

27. The apparatus of claim 25, wherein said analytical instrument is a liquid chromatograph.

28. The apparatus of claim 25, wherein said analytical instrument is a supercritical fluid chromatograph.

29. The apparatus of claim 1, further comprising means for fractionating the extract from said sample comprising valve means and thermal control means associated with said extraction section and said nozzle.

30. The apparatus of claim 1, further comprising a liquid trap connected to the nozzle, whereby the extraction fluid is expanded through the nozzle directly into the trap.

31. The apparatus of claim 4, wherein the nozzle comprises a variable orifice nozzle.

32. Apparatus for the extraction of components from a sample comprising:
   a pump for liquefying a gas to create a pressurized extraction fluid output stream;
   a pressure transducer for providing a signal to a means for controlling the pump to regulate the pressure of the output stream to a selected setpoint pressure;
   fluid conduit means for directing the output stream of said pump to an extraction chamber flow system comprising and extraction chamber for retaining a sample, and an outlet;
   a nozzle having a variable restriction orifice for limiting the mass flow rate of the pressurized fluid to a predetermined value, the nozzle connected to the extraction chamber flow system;
   whereby the pressure drop across the nozzle permits the recovery of dissolved material from the expanding pressurized extraction fluid.

33. The apparatus of claim 32, further comprising a liquid trap connected to the nozzle.

34. The apparatus of claim 32, further comprising an analytical instrument connected to the nozzle.

* * * * *